(12) United States Patent
Nessel et al.

(10) Patent No.: US 9,802,009 B2
(45) Date of Patent: Oct. 31, 2017

(54) NEEDLE MAGNETIZING ARRANGEMENT

(71) Applicant: SANOFI-AVENTIS DEUTSCHLAND GMBH, Frankfurt am Main (DE)

(72) Inventors: Christian Nessel, Frankfurt am Main (DE); Daniel Auernhammer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/441,293

(22) PCT Filed: Nov. 4, 2013

(86) PCT No.: PCT/EP2013/072898
§ 371 (c)(1),
(2) Date: May 7, 2015

(87) PCT Pub. No.: WO2014/072238
PCT Pub. Date: May 15, 2014

(65) Prior Publication Data
US 2015/0306319 A1    Oct. 29, 2015

(30) Foreign Application Priority Data
Nov. 8, 2012    (EP) ..................................... 12191829

(51) Int. Cl.
*A61M 5/50*    (2006.01)
*A61M 5/20*    (2006.01)
(Continued)

(52) U.S. Cl.
CPC ............ *A61M 5/5086* (2013.01); *A61M 5/20* (2013.01); *A61M 5/24* (2013.01); *A61M 5/32* (2013.01);
(Continued)

(58) Field of Classification Search
CPC ...... A61M 5/321; A61M 5/50; A61M 5/5086; A61M 2205/6054; A61M 5/20; A61M 5/24; A61M 5/32; A61M 2205/27; A61M 2205/273; A61M 2205/276; G11B 5/37; G11B 5/3912; G11B 5/3916; G11B 5/39
USPC .............................. 604/93.01, 111; 324/251
See application file for complete search history.

(56) References Cited

U.S. PATENT DOCUMENTS 3,741,198 A    6/1973    Burton
3,943,570 A *  3/1976    Yamamoto ............. G11B 5/376
                                                   324/251
(Continued)

FOREIGN PATENT DOCUMENTS

CN    1525833    9/2004
JP    H10-25658  1/1998
(Continued)

OTHER PUBLICATIONS

European Search Report issued in EP12191829 on May 8, 2013 (5 pages).
(Continued)

*Primary Examiner* — Imani Hayman
*Assistant Examiner* — James D Ponton
(74) *Attorney, Agent, or Firm* — Fish & Richardson P.C.

(57) ABSTRACT

A needle magnetizing arrangement (1) comprising a controller (4) adapted to generate a first magnetic field (F) for magnetizing a needle (2), and a magnetic field sensor (5) adapted to generate a signal based on a second magnetic field ($F_R$) of the needle (2).

18 Claims, 5 Drawing Sheets

(51) Int. Cl.
  *A61M 5/24* (2006.01)
  *A61M 5/32* (2006.01)
  *G11B 5/39* (2006.01)
  *G11B 5/37* (2006.01)

(52) U.S. Cl.
  CPC ..... *A61M 5/321* (2013.01); *A61M 2205/0272* (2013.01); *A61M 2205/273* (2013.01); *A61M 2205/6054* (2013.01); *G11B 5/37* (2013.01); *G11B 5/3912* (2013.01); *G11B 5/3916* (2013.01)

(56) References Cited

U.S. PATENT DOCUMENTS 4,447,233 A * 5/1984 Mayfield ........... A61M 5/14244
128/DIG. 12
2004/0073196 A1 * 4/2004 Adams ............. A61M 39/0208
604/890.1
2013/0116666 A1 * 5/2013 Shih .................. A61M 5/162
604/891.1

FOREIGN PATENT DOCUMENTS

| JP | H11-72479 | 3/1999 |
| WO | 02/40087 | 5/2002 |

OTHER PUBLICATIONS

International Search Report and Written Opinion issued in PCT/EP2013/072898 on Nov. 22, 2013 (9 pages).
International Preliminary Report on Patentability in International Application No. PCT/EP2013/072898, dated May 12, 2015, 6 pages.
Japanese Office Action in Application No. 2015-540144, dated Aug. 15, 2017, 9 pages.

* cited by examiner

NEEDLE MAGNETIZING ARRANGEMENT

This application is a 371 U.S. National Application of PCT/EP2013/072898, filed on Nov. 4, 2013, which claims priority to European Patent Application Nos. 12191829.6, filed on Nov. 8, 2012, the entire contents of which are incorporated herein by reference.

TECHNICAL FIELD

The invention relates to a needle magnetizing arrangement.

BACKGROUND OF THE INVENTION

In a conventional injection procedure, a user is generally advised to use a new injection needle or syringe for each injection to reduce a risk of cross contamination, infection and/or pain (e.g., when re-using blunt needles). However, the user may forget to change the needle or syringe before an injection thus subjecting themselves to the risks.

Some conventional injection devices utilize color coding to distinguish between used and unused injection needles and/or syringes. However, typically such color coding is in a small space on the injection device and can be difficult to see, especially for users with vision impairments.

In order to avoid these risks and overcome the problems associated with prior injection devices, there remains a need for a needle safety device, such as a needle magnetizing arrangement.

SUMMARY OF THE INVENTION

It is an object of the present invention to provide a needle magnetizing arrangement.

In an exemplary embodiment, a needle magnetizing arrangement according to the present invention comprises a controller adapted to generate a first magnetic field for magnetizing a needle, and a magnetic field sensor adapted to generate a signal based on a second magnetic field of the needle.

In an exemplary embodiment, the needle magnetizing arrangement further comprises a coil coupled to the controller. The controller passes current through the coil.

In an exemplary embodiment, the needle magnetizing arrangement further comprises a magnetic guide adapted to guide a flux of the second magnetic field toward the magnetic field sensor. The magnetic guide is coupled to the magnetic field sensor.

In an exemplary embodiment, the needle is coupled to a removably needle assembly or a syringe.

In an exemplary embodiment, the needle magnetizing arrangement further comprises a magnetic shield at least partially enclosing an area around the needle. The magnetic shield circumferentially encloses the area around the needle. The magnetic guide is enclosed by the magnetic shield. The magnetic shield is composed of Mu-metal, permalloy or electrical steel.

In an exemplary embodiment, the needle magnetizing arrangement further comprises a processor electrically coupled to the magnetic field sensor and adapted to receive the signal. The processor executes a predetermined action when the signal indicates a presence of the second magnetic field. The predetermined action is providing an audible or visual feedback.

In an exemplary embodiment, the arrangement is integrally formed with or removably coupled to an injection device. The predetermined action is preventing use of the injection device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
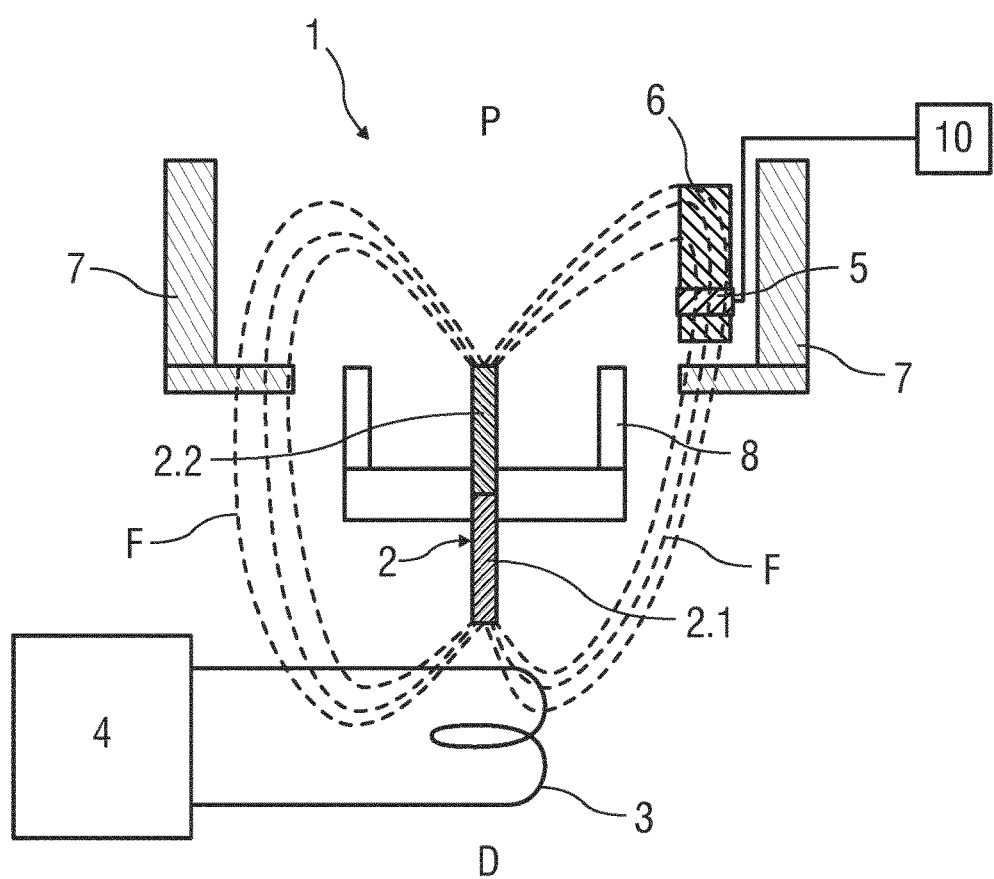
FIG. 1 is a schematic view of an exemplary embodiment of a needle magnetizing arrangement according to the present invention.

FIG. 1 is a schematic view of an exemplary embodiment of a needle magnetizing arrangement 1 according to the present invention. In an exemplary embodiment, the arrangement 1 is used to magnetize a needle 2 which is attached to a removable needle assembly 8. For example, the needle 2 may be a double-tipped needle in the needle assembly 8 which can be removably engaged (e.g., threaded) to a medicament delivery device and/or a medicament cartridge. In another exemplary embodiment, the needle 2 may be coupled to a syringe. Those of skill in the art will understand that the needle 2 may be coupled to any transcutaneous device.

In an exemplary embodiment, the needle magnetizing arrangement 1 comprises a controller 4 having a coil 3. When activated, the controller 4 passes a current through the coil 3 to generate a magnetic field for magnetizing the needle 2. Magnetizing the needle 2 may create magnetic poles 2.1, 2.2 on the needle 2, which exhibit a magnetic field F.

In an exemplary embodiment, the needle magnetizing arrangement 1 includes a magnetic field sensor 5 for determining a magnetic field strength of the needle 2 before and after the magnetization. A magnetic guide 6 disposed adjacent the sensor 5 may comprise a magnetically soft material for guiding a magnetic flux of the needle 2 to the magnetic field sensor 5. The guide 6 may thus focus and/or amplify the magnetic field strength detectable by the magnetic field sensor 5. A magnetic shield 7 may be arranged around the magnetic field sensor 5 and the needle 2 for limiting impact of ambient magnetic fields on the magnetic field sensor 5. For example, the magnetic shield 7 may enclose an area around the needle 2 and facilitate measurement of low magnetic field strengths.

In an exemplary embodiment, the sensor 5 may generate an electrical signal that is utilized by a processor 10 for taking a predetermined action. For example, if the signal indicates the needle 2 has been previously magnetized, the processor 10 may prevent an injection procedure from occurring, may provide a feedback to a user, etc. When a new, magnetically neutral needle is detected, the processor may allow an injection procedure, may provide a feedback to a user, etc.

In an exemplary embodiment, the arrangement 1 may be integrally formed with an medical device or may be removably coupled thereto. For example, the arrangement 1 may be utilized with a plurality of different medical devices which utilize needles or components having needles.

Figure 2:
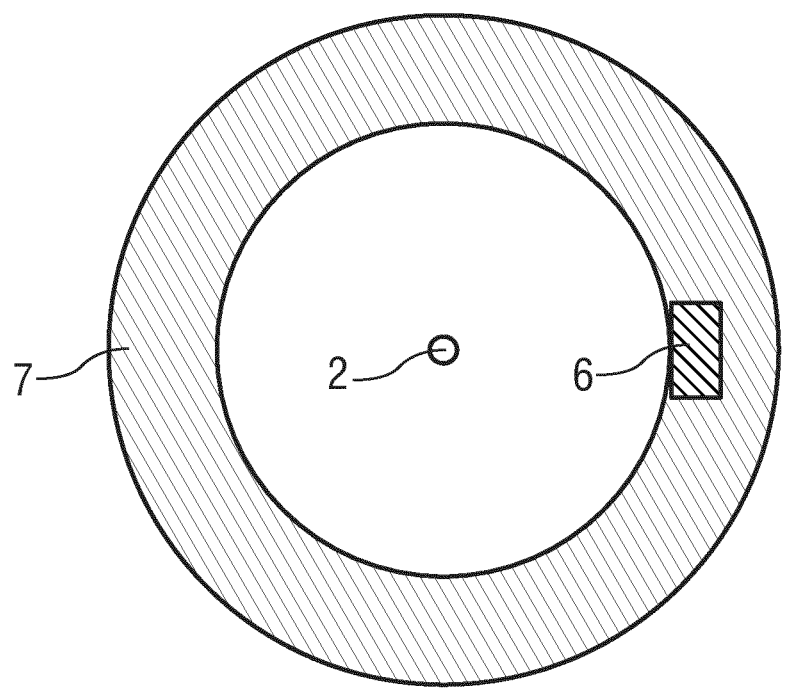
FIG. 2 is a schematic top cross sectional view of an exemplary embodiment of a needle magnetizing arrangement according to the present invention.

FIG. 2 is a schematic top cross sectional view of an exemplary embodiment of the needle 2, the magnetic shield 7 and the magnetic guide 6. In the exemplary embodiment, the shield 7 circumferentially encloses the needle 2 and the guide 6. This configuration may limit noise (e.g., due to ambient magnetic fields) in the signal generated by the sensor 5. In other exemplary embodiments, the shield 7 may partially enclose the needle 2. In another exemplary embodiment, the guide 6 may be embedded wholly or partially in the shield 7.

Figure 3:
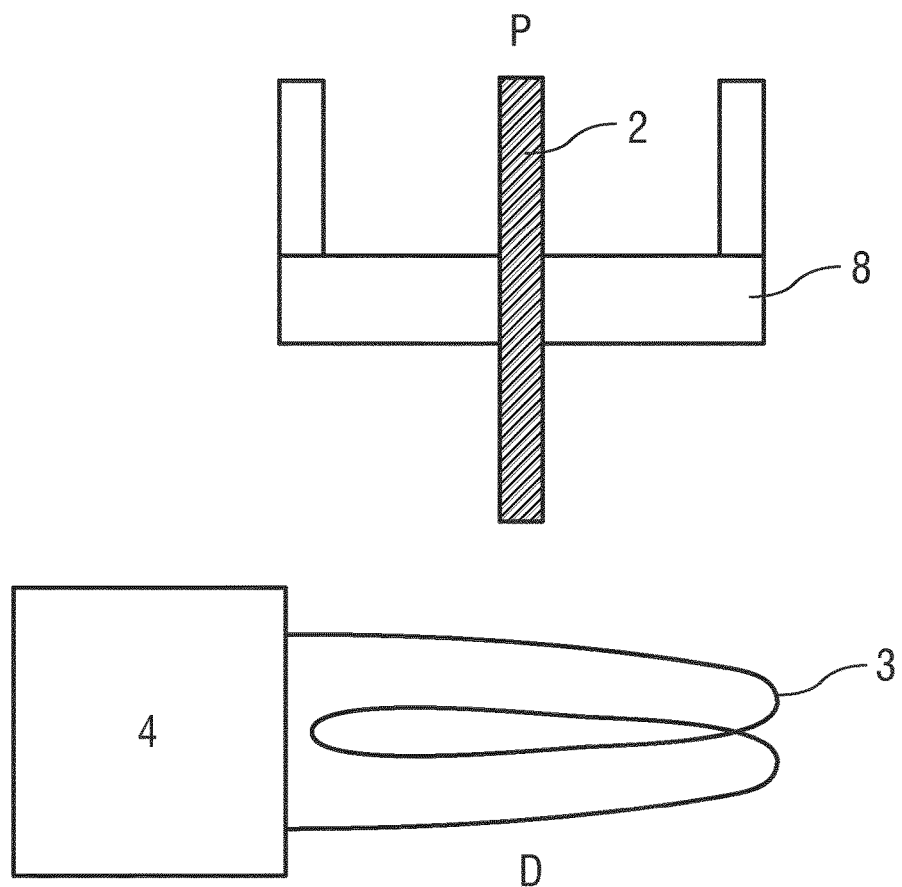
FIG. 3 is a schematic view of an exemplary embodiment of a needle magnetizing arrangement according to the present invention before use.

FIG. 3 is a schematic view of an exemplary embodiment of the needle magnetizing arrangement 1 prior to use. Prior to use, the needle 2 is magnetically neutral.

Figure 4:
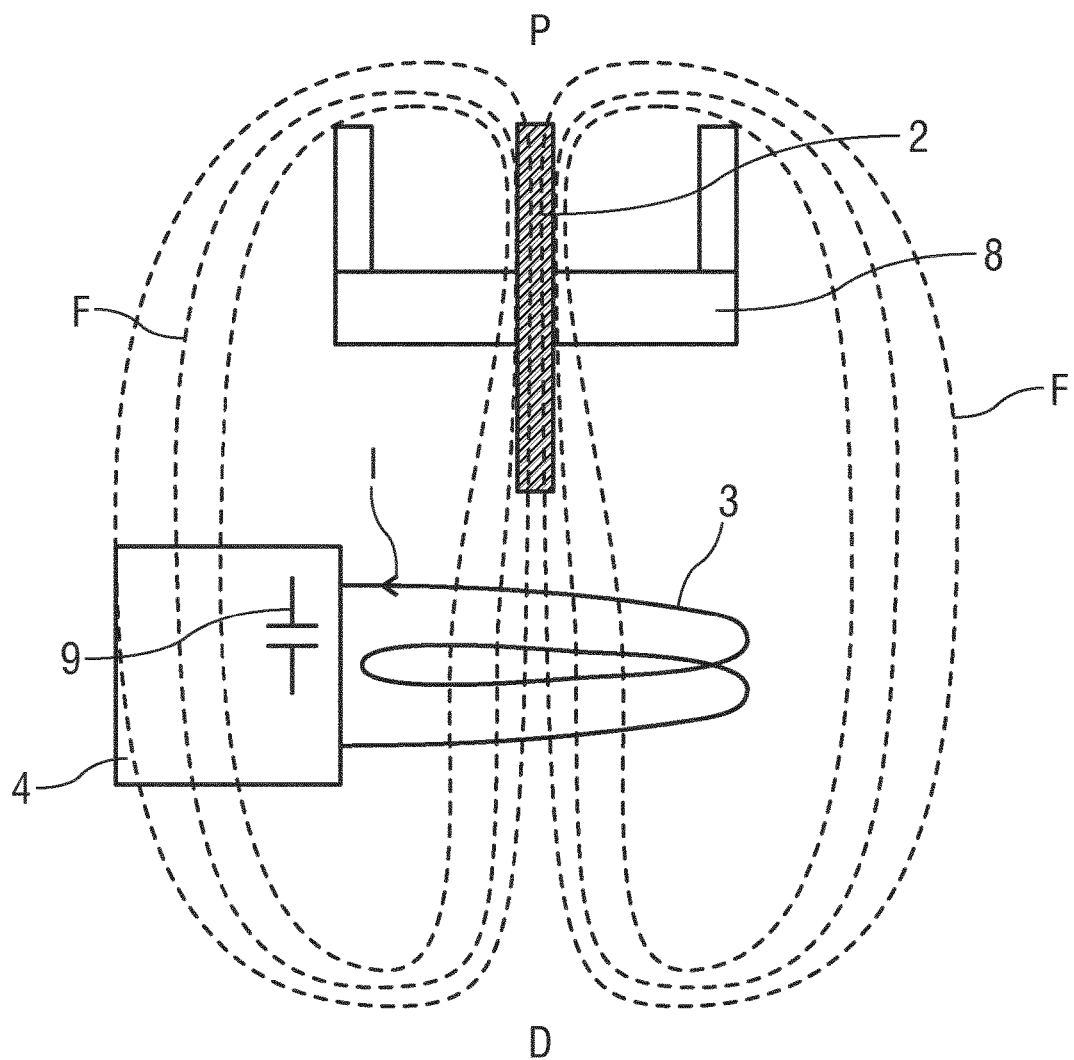
FIG. 4 is a schematic view of an exemplary embodiment of a needle magnetizing arrangement according to the present invention during use.
Figure 5:
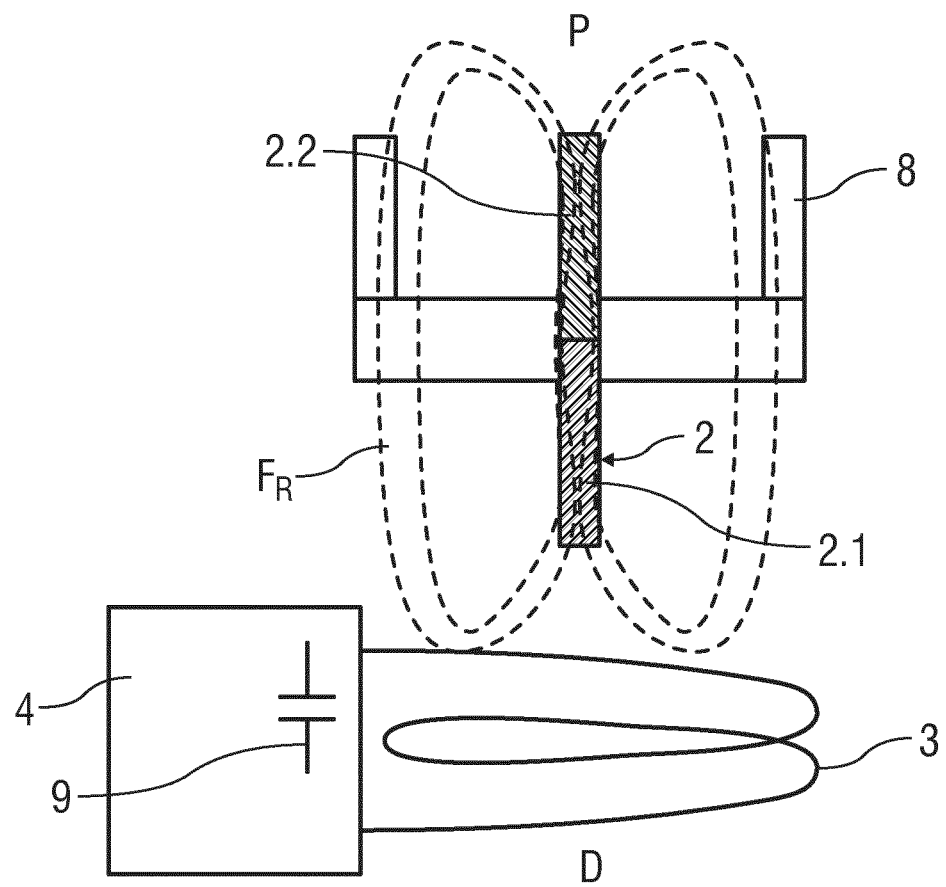
FIG. 5 is a schematic view of an exemplary embodiment of a needle magnetizing arrangement according to the present invention after use.

FIG. 4 is a schematic view of an exemplary embodiment of the needle magnetizing arrangement 1 during use. The magnetization controller 4 passes a current I through the coil 3 thereby generating a magnetic field F. In an exemplary embodiment, the magnetization controller 4 may generate the current I by discharging a capacitor 9. As the needle 2 is exposed to the magnetic field F, the needle 2 is magnetized, thus providing a magnetic orientation with a north pole 2.1 and a south pole 2.2. This magnetic orientation remains even after removing the magnetic field F by switching off the current I through the coil 3. Hence, the needle 2 has a permanent (or semi-permanent) magnetic field $F_R$ as illustrated in FIG. 5.

Those of skill in the art will understand that the current I may passed through the coil 3 in the opposite direction thereby switching the orientation of the magnetic field F and reversing the magnetic orientation of the needle 2.

Preventing re-use of needles may reduce the risk for causing the user pain when inserting a blunt needle and mitigate the risk of cross contamination by used non-sterile needles.

In an exemplary embodiment when using a needle 2 with a net magnetization of zero prior to use, the needle magnetizing arrangement 1 may be used to distinguish three different states of the needle 2 by detecting whether the net magnetization is different from zero and whether the north pole 2.1 points in a distal direction D or in a proximal direction P. The magnetization controller 4 may be arranged to accordingly magnetize the needle 2. In order to detect a direction of the magnetic field $F_R$ the magnetic field sensor 5 may for example be arranged as an XMR sensor using one of the magneto resistant quantum effects GMR (giant magneto resistance), AMR (anisotrope magneto resistance), CMR (colossal magnetor resistance), or TMR (tunnel magnetor resistance). If the direction of the magnetic field $F_R$ is irrelevant the magnetic field sensor 5 may also be a Hall sensor.

In another exemplary embodiment the magnetization controller 4 may be arranged to de-magnetize a magnetized needle 2 by driving an alternating current through the coil 3. In this case an unused needle 2 could have an initial net magnetization different from zero while a used needle would be marked by de-magnetizing it.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle magnetizing system comprising:
   a processor configured to:
      permit an injection procedure in response to determining an absence of a magnetic field in a first needle, wherein the absence of the magnetic field indicates that the first needle is unused; and
      prevent an injection procedure in response to determining a presence of a magnetic field in the first needle, wherein the presence of the magnetic field indicates that the first needle is used;
   a controller coupled to the processor, wherein, in response to the processor permitting the injection procedure in response to determining an absence of a magnetic field in a second needle, the controller is adapted to generate a first magnetic field (F) for magnetizing the second needle, wherein the first magnetic field (F) magnetizes the second needle to have a second magnetic field ($F_R$) during the injection procedure;
   a coil coupled to the controller, wherein the controller passes current (I) through the coil;
   a magnetic field sensor adapted to generate a signal based on the second magnetic field ($F_R$) of the second needle after it is magnetized by the first magnetic Field (F), wherein the second needle is positioned at a first distance from the coil, the first distance sufficient to magnetize the second needle to have the second magnetic field ($F_R$) and the magnetic field sensor is positioned at a second distance from the second needle, the second distance sufficient for the magnetic field sensor to sense the second magnetic field ($F_R$).

2. The needle magnetizing system according to claim 1 further comprising:
   a magnetic guide adapted to guide a flux of the second magnetic field ($F_R$) toward the magnetic field sensor.

3. The needle magnetizing system according to claim 2, wherein the magnetic guide is coupled to the magnetic field sensor.

4. The needle magnetizing system according to claim 1, wherein the second needle is coupled to a removable needle assembly or a syringe.

5. The needle magnetizing system according to claim 1 further comprising:
   a magnetic shield at least partially enclosing an area around the second needle.

6. The needle magnetizing system according to claim 5, wherein the magnetic shield circumferentially encloses the area around the second needle.

7. The needle magnetizing system according to claim 5, further comprising a magnetic guide adapted to guide a flux of the second magnetic field ($F_R$) toward the magnetic field sensor, wherein the magnetic guide is enclosed by the magnetic shield.

8. The needle magnetizing system according to claim 5, wherein the magnetic shield is composed of Mu-metal, permalloy or electrical steel.

9. The needle magnetizing system according to claim 1, wherein the processor is configured to perform a predetermined action in response to determining the presence of a magnetic field in the first needle, wherein the predetermined action is providing an audible or visual feedback.

10. The needle magnetizing system according to claim 1, wherein the system is integrally formed with or removably coupled to an injection device.

11. An injection device comprising:
an unmagnetized needle; and
a needle magnetizing system comprising:
 a processor configured to:
  permit an injection procedure in response to determining an absence of a magnetic field in a first needle, wherein the absence of the magnetic field indicates that the first needle is unused; and
  prevent an injection procedure in response to determining a presence of a magnetic field in the first needle, wherein the presence of the magnetic field indicates that the first needle is used;
 a controller coupled to the processor, wherein, in response to the processor permitting the injection procedure in response to determining an absence of a magnetic field in the unmagnetized needle, the controller is adapted to generate a first magnetic field (F) for magnetizing the unmagnetized needle, wherein the first magnetic field (F) magnetizes the unmagnetized needle; and
 a magnetic field sensor adapted to generate a signal based on a second magnetic field ($F_R$) of the needle magnetized by the first magnetic field (F), wherein the magnetic field sensor is positioned at a distance from the unmagnetized needle, the distance sufficient to sense the second magnetic field ($F_R$).

12. The injection device according to claim 11, wherein the needle magnetizing system further comprises:
a coil coupled to the controller, wherein the controller passes current (I) through the coil.

13. The injection device according to claim 11, wherein the needle magnetizing system further comprises:
a magnetic guide adapted to guide a flux of the second magnetic field ($F_R$) toward the magnetic field sensor; and
a magnetic shield circumferentially enclosing the unmagnetized needle and the magnetic guide.

14. A method comprising:
prior to using a first needle in a medicament injection procedure, wherein an unmagnetized needle is an unused needle and a magnetized needle is a used needle:
 positioning the first needle at a distance from a magnetic field sensor, the distance sufficient to sense any magnetic field in the first needle;
 measuring, by the magnetic field sensor, a magnetic field in the first needle, the magnetic field showing that the needle is magnetized; and
 in response to measuring the magnetic field, executing, by a processor, a predetermined action comprising preventing the injection procedure; and
in place of the first needle, positioning a second needle at the distance from the magnetic field sensor;
measuring, by the magnetic field sensor, no magnetic field in the second needle showing that the second needle is unmagnetized; and
in response to measuring no magnetic field in the second needle, executing, by the processor, the medicament injection procedure.

15. The method of claim 14, further comprising, after the medicament injection procedure magnetizing the second needle.

16. The method of claim 15, wherein magnetizing the second needle comprises:
generating, by a controller, a magnetic field by flowing a current through a coil; and
exposing the second needle to the generated magnetic field.

17. The method of claim 16, further comprising circumferentially enclosing an area around the second needle with a magnetic shield.

18. The method of claim 14, further comprising guiding a magnetic flux of the magnetic field in the first needle towards the magnetic field sensor using a magnetic guide.

* * * * *